US010022084B2

(12) United States Patent
Nonaka et al.

(10) Patent No.: US 10,022,084 B2
(45) Date of Patent: Jul. 17, 2018

(54) APPARATUS FOR DETERMINING RESPIRATORY CONDITION

(71) Applicants: NIHON KOHDEN CORPORATION, Tokyo (JP); National University Corporation Chiba University, Chiba-shi, Chiba (JP)

(72) Inventors: Yukio Nonaka, Tokyo (JP); Shiroh Isono, Chiba (JP); Tsuyoshi Shimizu, Tokyo (JP)

(73) Assignees: NIHON KOHDEN CORPORATION, Tokyo (JP); National University Corporation Chiba University, Chiba (JP)

( * ) Notice: Subject to any disclaimer, the term of this patent is extended or adjusted under 35 U.S.C. 154(b) by 453 days.

(21) Appl. No.: 14/316,143

(22) Filed: Jun. 26, 2014

(65) Prior Publication Data

US 2015/0005658 A1    Jan. 1, 2015

(30) Foreign Application Priority Data

Jun. 28, 2013  (JP) ................................ 2013-137019

(51) Int. Cl.
*A61B 5/00*         (2006.01)
*A61B 5/087*       (2006.01)
(Continued)

(52) U.S. Cl.
CPC ............ *A61B 5/4818* (2013.01); *A61B 5/085* (2013.01); *A61B 5/087* (2013.01); *A61B 5/097* (2013.01);
(Continued)

(58) Field of Classification Search
CPC ..... A61B 5/087; A61B 5/4818; A61B 5/0826; A61B 5/7239; A61B 5/7242
See application file for complete search history.

(56) References Cited

U.S. PATENT DOCUMENTS 5,335,654 A    8/1994   Rapoport et al.
5,490,502 A    2/1996   Rapoport et al.
(Continued)

FOREIGN PATENT DOCUMENTS

CA    2 245 869 C       8/2006
CA    2245869 C    *   8/2006   ............ A61M 16/00
(Continued)

OTHER PUBLICATIONS

Extended European Search Report dated Aug. 13, 2014 issued by the European Patent Office in counterpart European Patent Application No. 14173858.3.
(Continued)

*Primary Examiner* — Tiffany Weston
*Assistant Examiner* — Sarah Kingsley
(74) *Attorney, Agent, or Firm* — Sughrue Mion, PLLC

(57) ABSTRACT

An apparatus for determining a respiratory condition, including: a signal acquiring section which is configured to acquire a signal corresponding to a respiratory flow of a subject; a first index producing section which is configured to produce a first index related to the respiratory flow of the subject obtained from the signal; a second index producing section which is configured to produce a second index related to a respiratory demand of the subject predicted from the first index; a third index producing section which is configured to produce a third index related to a respiratory effort of the subject based on the first index and the second index; and an outputting section which is configured to output the third index.

4 Claims, 3 Drawing Sheets

(51) Int. Cl.
  *A61M 16/06* (2006.01)
  *A61B 5/085* (2006.01)
  *A61B 5/097* (2006.01)
  *A61M 16/00* (2006.01)

(52) U.S. Cl.
  CPC .......... *A61B 5/6819* (2013.01); *A61B 5/7242* (2013.01); *A61B 5/7278* (2013.01); *A61B 5/7282* (2013.01); *A61B 5/743* (2013.01); *A61B 5/746* (2013.01); *A61M 16/0672* (2014.02); *A61M 2016/0027* (2013.01); *A61M 2205/18* (2013.01)

(56) References Cited

U.S. PATENT DOCUMENTS

| | | |
|---|---|---|
| 5,535,739 A | 7/1996 | Rapoport et al. |
| 5,546,933 A | 8/1996 | Rapoport et al. |
| 5,803,066 A | 9/1998 | Rapoport et al. |
| 6,186,142 B1 * | 2/2001 | Schmidt ............... A61M 16/00 128/204.18 |
| 6,299,581 B1 | 10/2001 | Rapoport et al. |
| 6,475,156 B1 | 11/2002 | Vega |
| 6,488,634 B1 | 12/2002 | Rapoport et al. |
| 8,652,065 B2 * | 2/2014 | Titchener ............... A61B 5/087 600/538 |
| 2003/0055346 A1 | 3/2003 | Rapoport et al. |
| 2003/0111079 A1 | 6/2003 | Matthews et al. |
| 2004/0149282 A1 | 8/2004 | Hickle |
| 2004/0187870 A1 | 9/2004 | Matthews et al. |
| 2005/0016536 A1 | 1/2005 | Rapoport et al. |
| 2005/0256420 A1 | 11/2005 | Norman et al. |
| 2006/0000475 A1 | 1/2006 | Matthews et al. |
| 2006/0037614 A1 * | 2/2006 | Madaus ............... A61B 5/087 128/204.23 |
| 2007/0016093 A1 | 1/2007 | Rapoport et al. |
| 2008/0041382 A1 | 2/2008 | Matthews et al. |
| 2008/0041383 A1 | 2/2008 | Matthews et al. |
| 2009/0151719 A1 | 6/2009 | Wondka et al. |
| 2012/0152252 A1 | 6/2012 | Matthews et al. |
| 2013/0324877 A1 | 12/2013 | Nonaka et al. |

FOREIGN PATENT DOCUMENTS

| | | |
|---|---|---|
| CN | 101299963 A | 11/2008 |
| CN | 103445781 A | 12/2013 |
| EP | 2 668 900 A1 | 12/2013 |
| JP | 2000-504602 A | 4/2000 |
| JP | 2006-507905 A | 3/2006 |
| JP | 2010-540118 A | 12/2010 |
| JP | 5039041 B2 | 10/2012 |

OTHER PUBLICATIONS

Office Action dated Mar. 14, 2017, issued by Japanese Intellectual Property Office in counterpart Japanese Application No. 2013-137019.

Communication dated Feb. 26, 2018, issued by the State Intellectual Property Office of the People's Republic of China in counterpart Chinese application No. 201410302886.5.

\* cited by examiner

APPARATUS FOR DETERMINING RESPIRATORY CONDITION

CROSS-REFERENCE TO RELATED APPLICATION(S)

This application is based upon and claims the benefit of priority from prior Japanese patent application No. 2013-137019, filed on Jun. 28, 2013, the entire contents of which are incorporated herein by reference.

BACKGROUND

The presently disclosed subject matter relates to an apparatus for determining the respiratory condition of the subject in order to examine or monitor sleep respiratory disorder.

As one of apnea/hypopnea conditions occurring during sleep, there is obstructive apnea/hypopnea in which a respiratory effort is continued in an airway obstruction condition. In other words, when the respiratory effort of the subject is detected, it is possible to determine that sleep respiratory disorder occurs. A respiratory effort is recognized by measuring the airway pressure. There is an apparatus for determining the respiratory condition in which a sensor catheter is inserted into the esophagus of the subject to measure the airway pressure (for example, see JP-T-2010-540118).

In examination or monitoring of sleep respiratory disorder, it is required to perform a long-term overnight measurement. A long-term measurement in a state where catheter is inserted into the esophagus inevitably imposes significant botheration and burden on the subject. Under such a situation, the subject cannot sleep, and it is difficult to adequately perform a sleep test. For a person who performs diagnosis, on the other hand, a work of visually determining the respiratory condition of the subject from an enormous number of measurement signal waveforms which have been measured overnight causes a very large burden. In the case where the determination is performed based on visual observation, moreover, it is difficult to eliminate differences in determination results due to the subjectivity and experience of the observer.

SUMMARY

The presently disclosed subject matter may provide a technique which can determine sleep respiratory disorder correctly and easily while reducing botheration and burden of the subject.

An apparatus for determining a respiratory condition may comprise: a signal acquiring section which is configured to acquire a signal corresponding to a respiratory flow of a subject; a first index producing section which is configured to produce a first index related to the respiratory flow of the subject obtained from the signal; a second index producing section which is configured to produce a second index related to a respiratory demand of the subject predicted from the first index; a third index producing section which is configured to produce a third index related to a respiratory effort of the subject based on the first index and the second index; and an outputting section which is configured to output the third index.

The first index may be a signal waveform corresponding to the respiratory flow of the subject, and the second index may be a sinusoidal waveform, which is approximated so as to include: a first portion including a starting point of inspiration of the subject in the signal waveform; and a second portion indicating an ending point of inspiration of the subject, based on: a gradient of the first portion; and the second portion.

The third index producing section may be configured to set an amplitude of the sinusoidal waveform as the third index, and the third index may indicate a degree of the respiratory effort of the subject.

The apparatus may further comprise an integral value acquiring section which is configured to acquire an integral value of the sinusoidal waveform and an integral value of the signal waveform, between the inspiration starting point and the inspiration ending point, wherein the third index producing section may be configured to set a ratio of the integral value of the signal waveform to the integral value of the sinusoidal waveform, as the third index, and the third index may indicate a degree of attainment of ventilation due to the respiratory effort of the subject.

The apparatus may further comprise a displaying section which is configured to display the first index, wherein the outputting section may be configured to output the third index so as to be displayed synchronously with the first index on the displaying section.

The signal acquiring section may be configured to acquire the signal based on a respiratory pressure of the subject, which is output from a pressure sensor configured to measure the respiratory pressure.

The signal acquiring section may be configured to perform a square root correction on the signal.

The signal acquiring section may be configured to acquire the signal based on a respiratory gas which is introduced through a nasal cannula which is adapted to be attached to the subject.

The outputting section may be configured to output an alarm which is based on the third index.

DETAILED DESCRIPTION OF EXEMPLARY EMBODIMENTS

Hereinafter, an embodiment of the presently disclosed subject matter will be described in detail with reference to the accompanying drawings.

Figure 1:
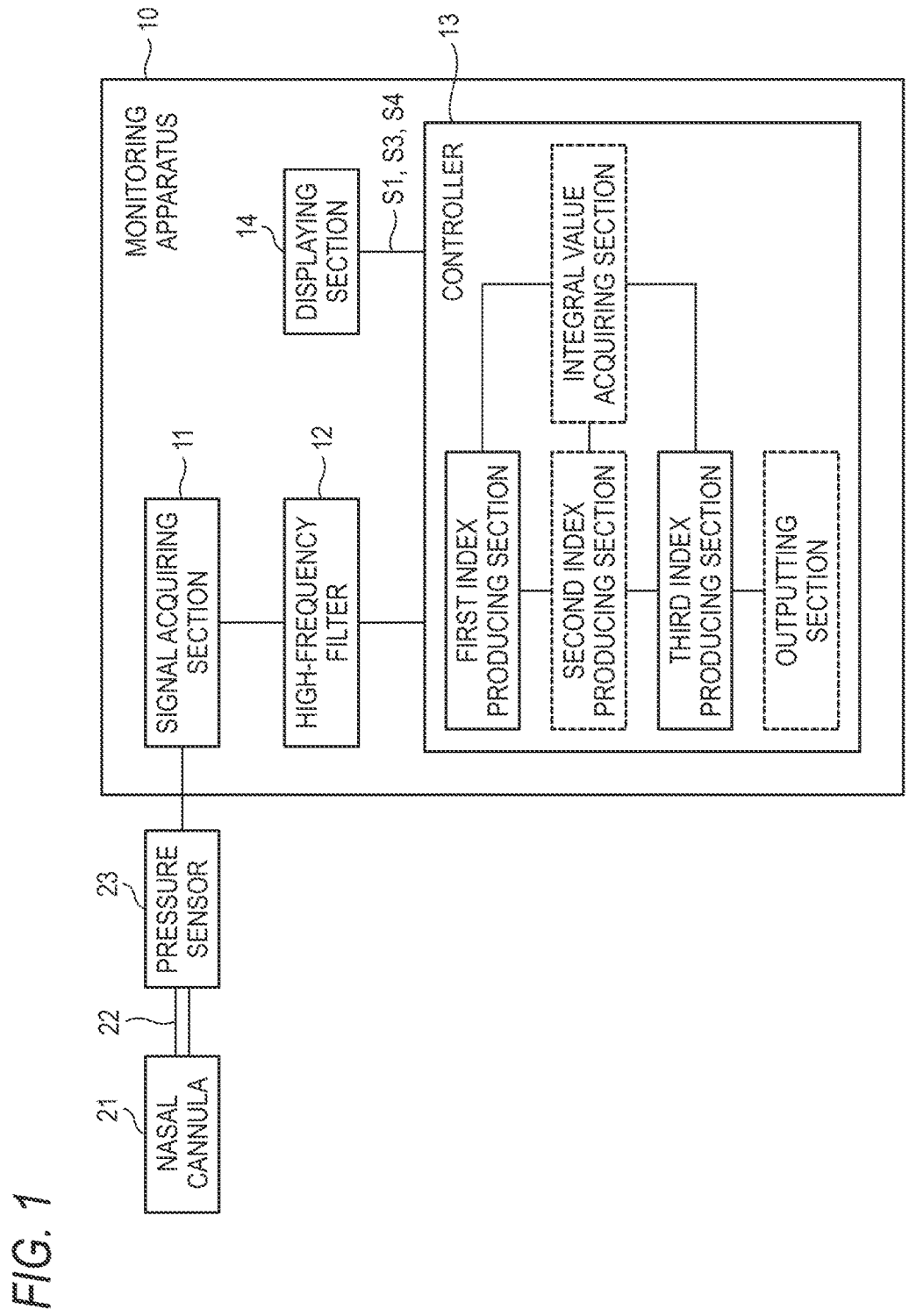
FIG. 1 is a functional block diagram showing the configuration of a monitoring apparatus of an embodiment of the presently disclosed subject matter.

FIG. 1 is a functional block diagram showing the configuration of a monitoring apparatus 10 which is an apparatus for determining the respiratory condition according to an embodiment of the presently disclosed subject matter. The monitoring apparatus 10 may include a signal acquiring section 11, a high-frequency filter 12, a controller 13, and a displaying section 14.

A nasal cannula 21 is a device in which a pair of pipe portions are to be inserted to the nostrils of the subject to guide the nasal respiratory gas of the subject to a pressure sensor 23 through a tube 22. The pressure sensor 23 is a sensor which measures a pressure change caused by respiration of the subject, and outputs a measurement signal having a waveform corresponding to the respiratory condition (respiratory pressure) of the subject (in following description, the signal is referred to merely as the measurement waveform).

Originally, it is preferable to determine the respiratory condition of the subject through measurement of the respiratory flow. However, such measurement requires a countermeasure for preventing the respiratory gas from leaking. By contrast, it is known that a good approximate value of the respiratory flow is obtained by multiplying the value of the respiratory pressure by a predetermined constant and then extracting the square root. This calculation process is referred to as the square root correction. In the embodiment, in order to more facilitate the measurement, the signal acquiring section 11 acquires a signal waveform S1 by performing the square root correction on the measurement waveform inputted from the pressure sensor 23.

The high-frequency filter 12 is an electrical filter which removes high-frequency components of the signal waveform S1 which is acquired by the signal acquiring section 11 by means of the square root correction. When components which are higher in frequency than a predetermined frequency are removed away, the signal waveform is smoothed, and the correctness of the calculation process which will be described later is improved. The signal which has passed through the high-frequency filter 12 is inputted to the controller 13.

The controller 13 may include: a CPU which performs various calculation processes; a ROM which stores various control programs; a RAM which is used as a working area for storing data and executing the programs; and the like, and performs various controls in the monitoring apparatus 10.

The controller 13 functions as an example of the first index producing section, and produces a signal waveform S1 from the signal inputted from the high-frequency filter 12. The signal waveform S1 which is an example of the first index shown in FIG. 2 indicates the respiratory flow of the subject obtained from the signal.

The inspiratory flow limitation is a phenomenon which is generated when the airway is obstructed during inspiration, and corresponds to a condition where, even when the patient wishes to breathe, the patient cannot breathe. As indicated by the broken line S2 in FIG. 2, in a normal condition, the respiratory pressure is lowered (the negative pressure is increased) as inspiration progresses. The signal waveform S1 in the figure shows a condition where inspiratory flow limitation occurs. As a result of inhibition of inspiration caused by airway obstruction, a phenomenon occurs in which the respiratory pressure is not lowered in a portion where the pressure should be originally lowered, but rather is raised.

The timing t1 when the value of the amplitude of the signal waveform S1 is changed from positive to negative is referred to as the inspiration starting point, and the timing t2 when the value is changed from negative to positive is referred to as the inspiration ending point. In this case, the waveform indicated by the broken line S2 corresponds to a part of a sinusoidal waveform which is approximated so as to start with a gradient that is equal to the gradient of the signal waveform S1 at the timing t1, and end at the timing t2.

The larger the gradient at the timing t1, the larger amplitude the approximated sinusoidal waveform S2 has. The fact that the gradient at the timing t1 is large corresponds to that in which the subject wants more strongly to perform inspiration. Therefore, the magnitude of the amplitude of the approximated signal waveform S2 can function as an index indicating the degree of the respiratory effort of the subject. It is said that a state where a strong respiratory effort is continuously performed is that where sleep apnea/hypopnea occurs. When the index is evaluated, therefore, it is possible to determine whether sleep respiratory disorder occurs in the subject or not.

The controller 13 is configured so as to acquire the approximated sinusoidal waveform S2 from the signal waveform S1 which corresponds to the respiratory flow acquired from the subject. Moreover, the controller 13 is configured so as to produce an index S3 relating to the respiratory effort of the subject based on the sinusoidal waveform S2. The process will be specifically described.

Figure 2:
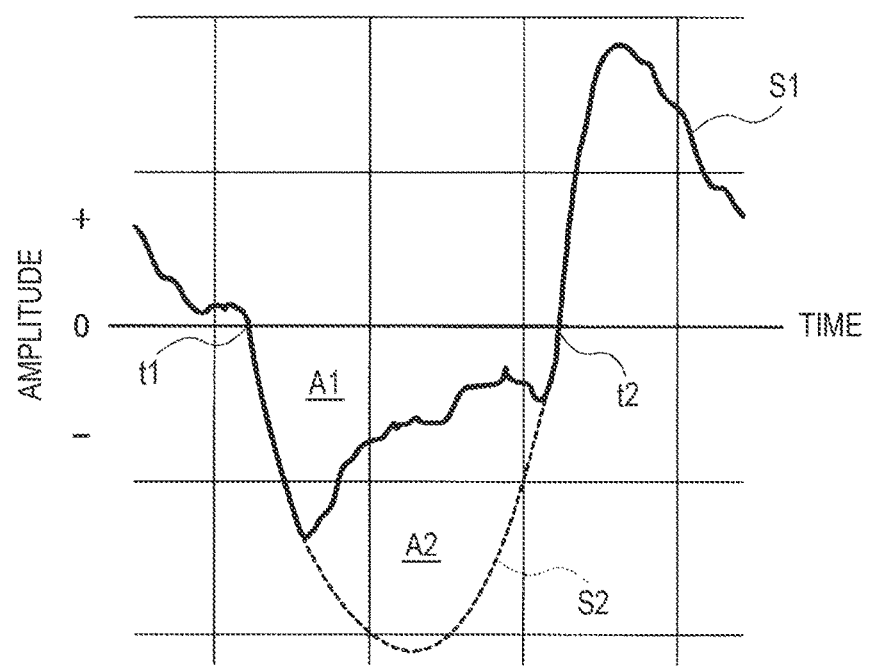
FIG. 2 is a view illustrating signal processing performed by the monitoring apparatus of FIG. 1.

First, the controller 13 identifies the timing t1 when the value of the amplitude of the signal waveform S1 in FIG. 2 is changed from positive to negative, and the timing t2 when the value is changed from negative to positive. As described above, the timing t1 indicates the inspiration starting point, and the timing t2 the inspiration ending point.

Next, the controller 13 functions as the second index producing section to acquire the gradient of the signal waveform S1 at the timing t1. Strictly speaking, the gradient of a first portion of the signal waveform S1 corresponding to a minute zone in which the timing t1 is the starting point is acquired. Then, the sinusoidal waveform S2 (an example of the second index) which is approximated so as to include the first portion and the timing t2 functioning as a second portion of the signal waveform S1 is acquired by calculation. Here, the term "include the first portion" means that the gradient of the signal waveform S1 at the timing t1 is equal to that of the approximated sinusoidal waveform S2.

Then, the controller 13 functions as the third index producing section to produce the amplitude of the sinusoidal waveform S2 as an index S3 (an example of the third index) indicating the degree of the respiratory effort of the subject. Furthermore, the controller 13 functions as the outputting section to output the index S3 together with the signal waveform S1 to the displaying section 14 (see FIG. 1). The controller 13 may output an alarm which is based on the index S3. The above expression "produce" means that data or signal corresponding to the manner of outputting the index S3 to the displaying section 14 are produced.

Figure 3:
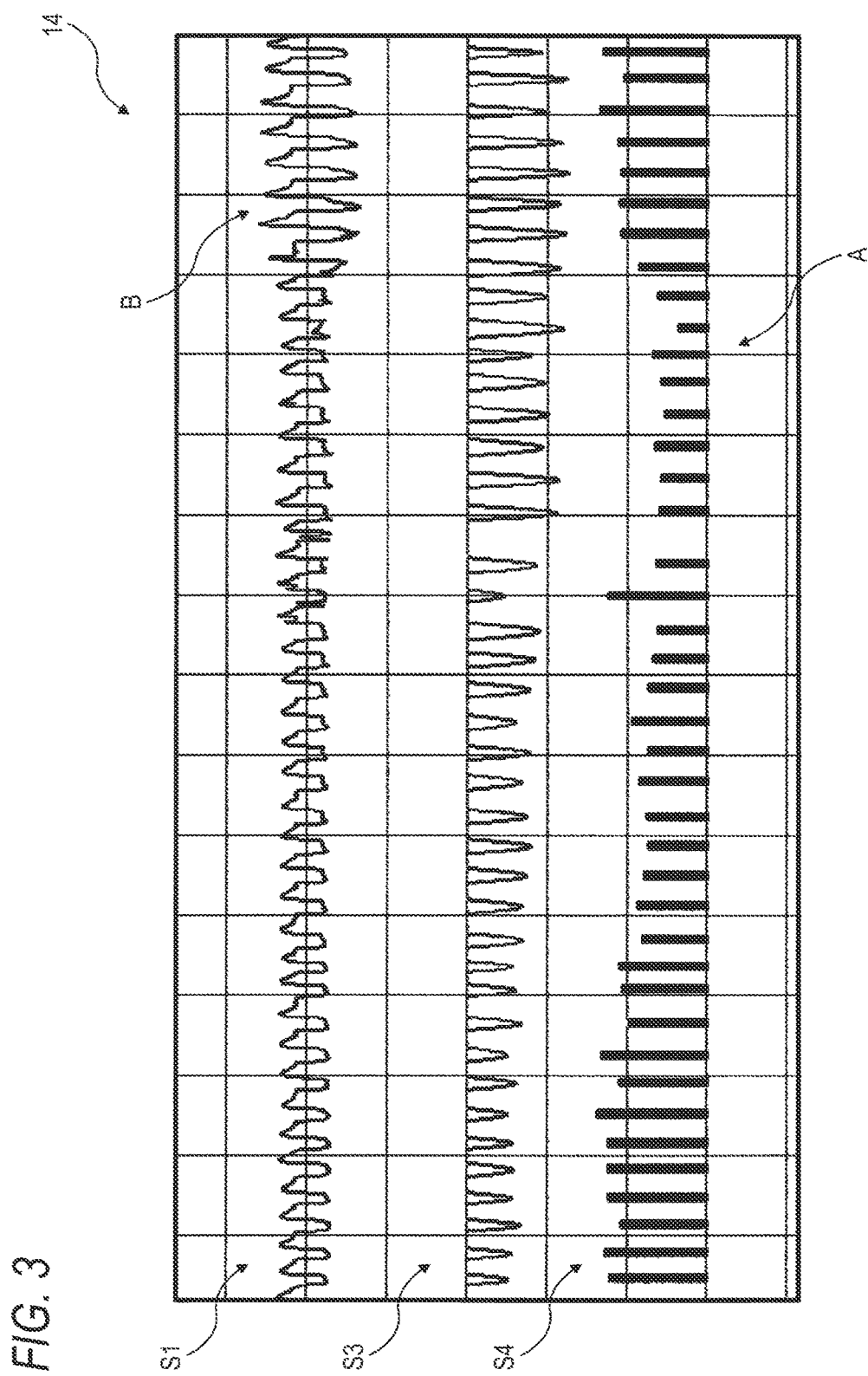
FIG. 3 is a view showing an example of a signal waveform displayed on a displaying section of the monitoring apparatus of FIG. 1.

FIG. 3 is a view showing a state where the signal waveform S1 and the index S3 are displayed in real time on the displaying section 14 including a display device. The figure shows that data are temporally newer with progression toward the right side of the figure. The controller 13 outputs the signal S1 and the index S3 to the displaying section 14 so that the index S3 is displayed temporally synchronously with the signal waveform S1. In the example, the index S3 is the sinusoidal waveform S2 itself which is approximated by the broken line in FIG. 2.

As seen from the figure, the amplitude of the signal waveform S1 and that of the index S3 do not always have positive correlation with each other. In the case where, although the respiratory effort, i.e., the amplitude of the index S3 is large, the respiratory flow, i.e., the amplitude of the signal waveform S1 is small, it is highly probable that the subject is in the obstructive apnea/hypopnea condition in which a respiratory effort is continued in an airway obstruction condition.

Even based only on the index S3 indicating the degree of the respiratory effort, it is possible to determine the occurrence of sleep respiratory disorder. In the case where a state where the amplitude of the index S3 is larger than a given value is continued for a predetermined period of time or longer, for example, it is possible to determine that sleep respiratory disorder occurs. When the index is displayed synchronously with the signal waveform S1 as shown in FIG. 3, even the kind of sleep respiratory disorder can be determined more correctly.

The mode of the index S3 is not limited to that shown in FIG. 3. For example, the controller 13 may be configured so as to perform processes of acquiring the maximum value of the amplitude of the approximated sinusoidal waveform S2 which is produced for each inspiration, producing a bar index having a length which corresponds to the magnitude of the value, and outputting the produced index to the displaying section 14. Alternatively, the controller 13 may be configured so as to perform processes of producing a symbol in which the color or the shape is changed in accordance with the magnitude of the value, and outputting the symbol to the displaying section 14.

The controller 13 may acquire the degree of attainment of the ventilation due to the respiratory effort of the subject, as the index relating to the respiratory effort. The degree of attainment of the ventilation is expressed as a ratio of the amount of ventilation which was able to actually be performed, to the amount of ventilation which is originally required by the subject oneself.

When the controller 13 acquires the above-described degree of attainment of the ventilation as an index in addition to the index indicating the degree of the respiratory effort, it is possible to analyze and acquire in more detail the condition of sleep respiratory disorder of the subject.

Specifically, the controller 13 functions as an example of the integral value acquiring section to acquire integral values of the signal waveform S1 and the approximated sinusoidal waveform S2 between the inspiration starting point t1 and the inspiration ending point t2. In the example shown in FIG. 2, the area A1 of the signal waveform S1 which exists below the time axis, and the area A2 of the approximated sinusoidal waveform S2 are acquired.

In the embodiment, the integral value of the approximated sinusoidal waveform S2 (i.e., the area A2) is deemed as the amount of ventilation which is originally required by the subject. By contrast, the integral value of the signal waveform S1 (i.e., the area A1) indicates the amount of ventilation which was able to actually performed. When the ratio of the area A1 to the area A2 is calculated, therefore, the degree of attainment of the ventilation can be acquired. The controller 13 functions as the third index producing section to produce the area ratio A1/A2 (the ratio of integral values) as an index S4 (an example of the third index) indicating the degree of attainment of the ventilation.

The controller 13 outputs the produced index S4 to the displaying section 14 so that the index S4 is displayed temporally synchronously with the signal waveform S1 and the index S3 as shown in FIG. 3. Here, a bar index having a length corresponding to the value of the ratio which is obtained by the calculation is produced. Alternatively, another configuration may be employed where a symbol in which the color or the shape is changed in accordance with the value of the ratio is produced, and then displayed.

According to the configuration, the signal waveform S1 corresponding to the respiratory flow of the subject, the index S3 indicating the degree of the respiratory effort, and the index S4 indicating the degree of attainment of the ventilation are displayed on the displaying section 14. When a medical person adequately compares them to one another, it is possible to determine in detail and compositely the respiratory condition of the subject. In the time domain indicated by the reference letter A in FIG. 3, for example, it is seen that the degree of attainment of the ventilation is relatively low. In the succeeding time domain indicated by the reference letter B, the signal waveform S1 of a large amplitude can be seen, and it is presumed that this is arousal caused for ensuring ventilation. Moreover, each of the indexes is produced based on the constant criterion. Therefore, the respiratory condition of the subject can be determined easily and correctly without visually observing a measurement waveform. Consequently, the determination result is highly reliable.

According to the monitoring apparatus 10 of the embodiment, the determination of the respiratory condition of the subject through the above-described series of processes can be performed simply by measuring the respiratory pressure of the subject. It is not necessary to insert a sensor catheter which directly measures the airway pressure, into the esophagus, and therefore botheration and pain which may be felt by the subject can be reduced. In the embodiment, particularly, only the nasal cannula which is small in size, and which is relatively light in weight is attached to the subject, and therefore interference with sleep can be suppressed. For a person who performs diagnoses, on the other hand, the index indicating the degree of attainment of the ventilation functions as an objective index of the determination result, and moreover it is possible to easily identify a problematic waveform from an enormous number of measurement signal waveforms which have been measured overnight.

The above-described functions of the controller 13, i.e., those as the first to third index producing sections, the integral value acquiring section, and the outputting section can be realized by the operation of hardware such as circuit devices constituting the controller 13, that of software such as programs stored in an arithmetic device, or a combination of these operations.

The embodiment has been described in order to facilitate understanding of the presently disclosed subject matter, and is not intended to limit the presently disclosed subject matter. It is a matter of course that the presently disclosed subject matter may be changed or improved without departing the spirit thereof, and includes equivalents thereof.

The inspiration starting point t1 and inspiration ending point t2 shown in FIG. 2 are not always required to be points where the sign of the amplitude of the signal waveform S1 is switched. The points may be adequately set as far as they comply with given requirements.

It is not always necessary to acquire and output both of the indexes S3, S4. Alternatively, a configuration may be employed where only one of the indexes which is required for determining the respiratory condition of the subject is acquired and output.

The "output" of the indexes S1, S3, S4 from the controller 13 is not limited to that for the purpose of displaying on the displaying section 14. Alternatively, for example, the output may be performed for the purpose of printing in a printer which is not shown, or for the purpose of storing in a storage device which is not shown. In the alternatives, the controller 13 produces the indexes S1, S3, S4 in the form of signals or data according to the purpose, and transmits the indexes toward an output target apparatus. In the case where the output target apparatus is a ventilator, settings and the like can be changed in accordance with the transmitted indexes.

It is not always necessary to dispose the pressure sensor 23 outside of the main unit of the monitoring apparatus 10. Alternatively, the pressure sensor may be configured so as to be incorporated in the monitoring apparatus 10 as a component which constitutes a part of the signal acquiring section 11.

A respiration flow sensor or a temperature sensor may be used in place of the pressure sensor 23 as far as the alternative sensor can measure a signal waveform corresponding to the respiratory condition of the subject.

The signal waveform which is inputted to the signal acquiring section 11, and which corresponds to the respiratory condition of the subject is not necessary to be the measurement waveform of the respiratory pressure of the subject. A configuration may be employed where the measurement waveform of the respiratory flow of the subject is directly inputted to the signal acquiring section 11. In this case, the process of square root correction in the signal acquiring section 11 is not required.

The device which guides the respiratory gas of the subject to the pressure sensor 23 or the monitoring apparatus 10 is not limited to the nasal cannula 21. In addition to or in place of this, a mask which covers the mouth of the subject may be used.

The displaying section 14 is not always required to be disposed as a part of the monitoring apparatus 10. A configuration may be employed where a displaying device which is disposed outside the monitoring apparatus 10, and which is communicably connected to the controller 13 functions as the displaying section 14.

Since the apparatus for determining the respiratory condition, includes: a signal acquiring section which is configured to acquire a signal corresponding to a respiratory flow of a subject; a first index producing section which is configured to produce a first index related to the respiratory flow of the subject obtained from the signal; a second index producing section which is configured to produce a second index related to a respiratory demand of the subject predicted from the first index; a third index producing section which is configured to produce a third index related to a respiratory effort of the subject based on the first index and the second index; and an outputting section which is configured to output the third index, the index relating to the respiratory effort can be obtained from the signal corresponding to the respiratory flow of the subject. It is not necessary to insert a sensor catheter which directly measures the airway pressure, into the esophagus. Therefore, botheration and burden imposed on the subject can be reduced.

By referring to the index which is produced based on the constant criterion, the respiratory condition of the subject can be determined easily and correctly without visually observing a measurement waveform. Therefore, the determination result is highly reliable.

Since the apparatus further includes a displaying section which is configured to display the first index, and the outputting section is configured to output the third index so as to be displayed synchronously with the first index on the displaying section, when the first and third indexes are adequately compared to each other, the respiratory condition of the subject can be determined in detail and compositely.

The signal acquiring section may acquire the signal based on a respiratory pressure of the subject, which is output from a pressure sensor configured to measure the respiratory pressure. In this case, a simpler measurement is enabled as compared with the case where the respiratory flow of the subject is measured.

When the signal acquiring section performs a square root correction on the measurement waveform, an approximate value of the respiratory flow can be accurately obtained.

The signal acquiring section may acquire the signal based on a respiratory gas which is introduced through a nasal cannula which is adapted to be attached to the subject. In this case, it is not necessary to attach various kinds of sensors to the body, and therefore botheration and burden which may be felt by the subject can be reduced. Particularly, the nasal cannula is relatively light in weight, and therefore interference with sleep can be suppressed.

What is claimed is:

1. An apparatus for determining a respiratory condition, the apparatus comprising:
    a display;
    a memory configured to store computer-readable instructions; and
    a processor configured to execute the computer-readable instructions, which when executed cause the processor to execute a method of determining respiratory condition of a subject, the method comprising:
        receiving a signal corresponding to a respiratory flow of the subject;
        calculating a signal waveform corresponding to the respiratory flow of the subject based on the signal, wherein the calculating the signal waveform comprises:
            performing a square root correction on the signal corresponding to the respiratory flow of the subject; and
            smoothing the corrected signal using a high-frequency filter to remove components of the corrected signal greater in frequency than a predetermined frequency;
        calculating a sinusoidal waveform corresponding to a respiratory demand of the subject predicted from the signal waveform, wherein the calculating the sinusoidal waveform comprises:
            determining a first timing at which a value of amplitude of the signal waveform is changed from positive to negative as an inspiration starting point;
            determining a gradient of the signal waveform at the first timing;
            determining a second timing at which the value of the amplitude of the signal waveform is changed from negative to positive as an inspiration ending point; and
            approximating a part of the sinusoidal waveform to start with a gradient that is equal to the gradient of the signal waveform at the first timing and ending at the second timing;
        calculating respiratory effort of the subject based on the sinusoidal waveform by setting an amplitude of the sinusoidal waveform as the respiratory effort of the subject;
        calculating an integral value of the sinusoidal waveform and an integral value of the signal waveform, between the inspiration starting point and the inspiration ending point;
        setting a ratio of the integral value of the signal waveform to the integral value of the sinusoidal waveform, as a degree of attainment of ventilation of the subject; and
        controlling the display to synchronously display the signal waveform and the respiratory effort, wherein the step of controlling the display comprises synchronously displaying the signal waveform, the respiratory effort, and the degree of attainment of ventilation, and
    wherein the sinusoidal waveform is approximated to include:
        a first portion including the inspiration starting of the subject in the signal waveform and a second portion indicating the inspiration ending point of the subject, based on: (i) a gradient of the first portion and (ii) the second portion.

2. The apparatus according to claim 1, wherein the received signal corresponding to the respiratory flow of the subject based on a respiratory pressure of the subject output from a pressure sensor configured to measure the respiratory pressure.

3. The apparatus according to claim 1, wherein the received signal corresponding to the respiratory flow of the subject is based on a respiratory gas introduced through a nasal cannula adapted to be attached to the subject.

4. The apparatus according to claim 1, wherein the method further comprises outputting an alarm based on the respiratory effort of the subject.

* * * * *